(12) United States Patent
Perricone

(10) Patent No.: US 6,472,432 B1
(45) Date of Patent: Oct. 29, 2002

US006472432B1

(54) TREATMENT OF ROSACEA USING LIPOIC ACID

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 09/415,792

(22) Filed: Oct. 8, 1999

Related U.S. Application Data

(63) Continuation-in-part of application No. 08/971,820, filed on Nov. 17, 1997, now Pat. No. 5,965,618.

(51) Int. Cl.$^7$ .................. A61K 31/20; A61K 31/19; A61K 31/355; A61K 31/385
(52) U.S. Cl. ................. 514/558; 514/557; 514/458; 514/440
(58) Field of Search ................ 514/440, 458, 514/558, 557

(56) References Cited

U.S. PATENT DOCUMENTS

| | | | |
|---|---|---|---|
| 5,084,481 A | * 1/1992 | Ulrich et al. ............... | 514/557 |
| 5,472,698 A | 12/1995 | Rawlings et al. ........... | 424/401 |
| 5,545,398 A | * 8/1996 | Perricone .................... | 424/59 |
| 5,569,670 A | 10/1996 | Weischer et al. ........... | 514/440 |
| 5,693,664 A | 12/1997 | Wessel et al. ............... | 514/440 |
| 5,972,993 A | * 10/1999 | Ptchelintsev ................ | 514/449 |

FOREIGN PATENT DOCUMENTS

| | | | | |
|---|---|---|---|---|
| WO | WO 95/16454 | * | 6/1995 | .......... A61K/31/74 |

* cited by examiner

*Primary Examiner*—Russell Travers
(74) *Attorney, Agent, or Firm*—St. Onge Steward Johnston & Reens LLC

(57) ABSTRACT

Rosacea is treated by application of a composition containing lipoic acid and/or a lipoic acid derivative such as dihydrolipoic acid, a lipoic or dihydrolipoic acid ester, a lipoic or dihydrolipoic acid amide, a lipoic or dihydrolipoic acid salt, and mixtures of any of these. Preferred compositions further comprise α-hydroxy acids or acid derivatives such as glycolic and/or lactic acid. Other embodiments also contain fatty acid esters of ascorbic acid such as ascorbyl palmitate, and/or tocotrienol.

13 Claims, No Drawings

TREATMENT OF ROSACEA USING LIPOIC ACID

CROSS-REFERENCES TO RELATED APPLICATIONS

This application is a continuation-in-part of U.S. application Ser. No. 08/971,820, filed Nov. 17, 1997, now issued U.S. Pat. No. 5,965,618 issued Nov. 17, 1997 which is incorporated herein by reference.

STATEMENT REGARDING FEDERALLY SPONSORED RESEARCH

Not Applicable

BACKGROUND OF THE INVENTION

1. Field of the Invention

This invention relates primarily to methods and compositions for the treatment of rosacea. Rosacea is a chronic inflammatory disorder affecting the blood vessels and pilosebaceous units of the face in middle-aged individuals, afflicting as many as 13 million Americans. Patients with rosacea have papules and pustules superimposed on diffuse erythema and telangiectasia (visible blood vessels) over the central portion of the face. Hence, the clinical features are facial redness, swelling, papules, pustules, and telangiectasias. An important component of the patients' history is often easy flushing and blushing of the face, and this is often accentuated when alcohol, caffeine-containing, or hot spicy foods are ingested. Hyperplasia of the sebaceous glands, connective tissue, and vascular bed of the nose sometimes causes rhinophyma, or a large, red, bulbous nose in addition to the other signs. Ocular complications occur in a small but significant number of rosacea patients; these include blepharitis, chalazion, conjunctivitis, and keratinitis. Progressive keratinitis can lead to scarring and blindness.

Rosacea and the eye complications are usually responsive to tetracycline, but the antibiotic must be continued for life (at the lowest dose that suppresses the condition) because rosacea recurs when therapy is interrupted. In addition to the undesirability of the more prevalent use of antibiotics in general, a disadvantage to such treatments are the possible side effects associated with long-term use of oral antibiotics, such as nausea, gastrointestinal upset, phototoxicity, enhanced susceptibility to yeast infection, and interactions with other medications. Oral antibiotics may also lessen the effectiveness of oral contraceptives. High-potency topical corticosteroid preparations may induce or aggravate pre-existing rosacea and should not be used for long periods of time on the face. Instead, topical metronidazole is sometimes prescribed for reducing skin redness and the number of pimples on the face of patients with rosacea. Laser therapy has been used to reduce the telangiectasia and redness in some cases. (See Wilkin J K: Rosacea: Pathophysiology and Treatment. *Archives of Dermatology*, 1994, 130:359–362; this and subsequent references are expressly incorporated herein by reference.) It would be desirable to have alternate treatments for rosacea.

2. Description of Related Art

Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Subsequent research showed that lipoic acid (LA) was a growth factor for many bacteria and protozoa, and it served as a prosthetic group, coenzyme, or substrate in plants, microorganisms, and animal tissues. Elucidation of its structure and function determined that it is a co-factor for α-keto-dehydrogenase complexes, typically bound as lipoamide, that participates in acyl transfer reactions. Its reduced form, dihydrolipoic acid (DHLA), is a potent sulfhydryl reductant. In aqueous systems, both LA and DHLA exhibit antioxidant actions (reviewed by Packer, L., et al., *Free Rad. Biol. Med.,* 1995, 19: 227–250 (1995)). LA has been shown to maintain microsomal protein thiols, protect against hemolysis, and protect against neurological disorders. The protective effect of dietary supplementation of LA against ischemia/reperfusion injury in the Langendorff isolated heart model has also been demonstrated. LA has been suggested for treating systemically, or as adjuvant systemic medication for, liver cirrhosis, atheroschlerosis, diabetes, neurodegenerative diseases, heavy metal poisoning, and Chagas disease (ibid.). It has also been used as an antidote to poisonous mushrooms (ibid., particularly Amanita species, *Merck Index,* 11th ed., 1989, entry 9255).

Few references suggest the use of lipoic acid in dermatological compositions. In a 1988 Japanese patent publication (JP 63008315), lipoic acid in cosmetics at concentrations of 0.01% to 1%, preferably 0.05% to 0.5%, or in topical "quasi-drugs" at concentrations of 0.1% to 1.5%, preferably 0.5% to 1.0%, were suggested for inhibiting tyrosinase, and thus melanin formation, to whiten skin.

In 1995, Rawlings, et al., disclosed a composition and method for "improving or preventing the appearance of dry, flaky wrinkled, aged, photodamaged skin and treating skin disorders" (U.S. Pat. No. 5,472,698, column 2, lines 51 to 54) using a synergistic combination of serine and/or N-acetyl serine and a thiol, an "S-ester", and/or a disulfide (id., lines 28 to 33). Lipoic acid was mentioned as encompassed by the latter ingredient (column 3, lines 29 to 30). However, the patent's terminology was confusing. Thiols and S-esters were disclosed as preferable over disulfides (column 4, lines 1 to 4). Though lipoic acid is a disulfide, it's listed as a thiol in the patent (column 3, lines 29 to 30); perhaps what is referred to as "lipoic acid" is, instead, dihydrolipoic acid. This supposition is reinforced by the fact that a Sigma product was employed in some examples (column 7, line 63). Both oxidized lipoic acid and reduced, i.e., dihydrolipoic acid, are available from that chemical company, so DHLA may have been used. Unfortunately, there is more uncertainty about the effects of DHLA when compared to LA (see Packer, et al., cited above, 231–234). The only illustrations of alternate sulfur-containing ingredients were acylated cysteine derivatives, including glutathione.

More importantly, the focus of the patent was stimulation of sphingolipid synthesis in skin to improve it (see column 1 at lines 21 to 23 and column 2 at lines 12 to 13). The examples reported that assays monitored ceramide production in cultured human keratinocytes and porcine skin. In the studies, lipoic acid had no effect in compositions without serine. On the contrary, in every reported assay, the lipoic acid values were identical to controls; see Tables 2 and 3. And, though increasing concentrations of lipoic in the presence of a constant amount of serine boosted ceramide production at certain levels of serine (Table 7), other thiols worked equally well (Tables 1, 4, 5, 6, 8, and 9). Read as a whole, the reference teaches away from LA as an active ingredient, and suggests DHLA of efficacy only with serine or N-acetyl serine.

A year later, in U.S. Pat. No. 5,569,670 to Weischer, et al., pharmaceutical compositions containing a synergistic combination of α-lipoic acid and/or dihydrolipoic acid with specific enantiomers of these, together with some vitamins, including C and E (column 1, lines 3 to 15), were disclosed as useful, primarily for treating diabetes (see the claims). However, anti-inflammatories (abstract, line 8 and column 2 at line 16) as well as treatments for retroviruses and other pathological conditions were included, with an emphasis on veterinary applications (column 13, lines 42 to 62). In a test model for inflammation (observing rat edema), the R-enantiomer of lipoic acid was superior to lipoic alone or to vitamin E alone (column 3, lines 37 to 40). Suggested administration was oral, parenteral or intravenous (column 7, line 31 to end, et seq.), preferably oral (column 11, line 42), but application to skin and mucous membranes was mentioned (column 12, lines 58 to 60). Antioxidants could be employed in some embodiments (column 16, lines 47 to 55), and the list included ascorbic acid, ascorbyl "palmirate" [sic] and tocopherols. The examples combined lipoic and/or dihydrolipoic acid with tocopherols (Examples 1, 2, 5, and 6) or ascorbic acid (Examples 3, 4, and 7). An ointment was disclosed in Example 6; the others described suppositories, capsules, ampules, and tablets.

Similarly, U.S. Pat. No. 5,693,664 to Wessel, et al., from the same research group, was directed to diabetes treatments, particularly where insulin resistance is observed (column 1, lines 10 to 14 and the claims) by use of the R-enantiomer of α-lipoic acid. Again, one enantiomer, not a racemate, was employed (column 6, lines 18 to 19). Indeed, the S-enantiomer decreased the effect of insulin in an experimental study reported (column 3, lines 61 to 65). Suggested adminstration was primarily oral (column 6, lines 61 to 66), though parenteral and intravenous are mentioned (ibid., and column 3, lines 7 to 8).

U.S. Pat. No. 5,728,735 to Ulrich, et al., again from the same group, stressed use of an enantiomer (column 1, lines 28 to 54), particularly the R-enantiomer (see the claims), and not a racemate, for combatting pain and inflammation in a variety of conditions (id., lines 58 to 59; inflammations are listed in column 5, line 64 to column 6, lines 9 and include neurodermatitis and psoriasis). Suggested administrations were oral, intravenous, or infusions (column 3, lines 28 to 30, 51, 62 to 63 and 65), but solutions and emulsions for topical application were mentioned (column 6, lines 29 to 34 and 65 to 68, and column 8, lines 16 to 18). Only tablets and ampules were illustrated. All the reported findings of the group are complicated by the fact that the metabolic effects of the R- and S-enantiomers are now known to be different, as are the enzymes that process the enantiomers in cytosolic and mitrochondrial systems (Haramaki, N., et al., *Free Rad. Biol. Med.* 22: 535–542 (1997)). Moreover, different stereospecific reduction by intact cells and tissues has also been observed (ibid.).

More recently, Perricone suggested the use of lipoic acid in dermatological compositions for the treatment of skin damage, particularly inflammation and aging (U.S. Pat. No. 5,709,868). As explained in that reference, the antioxidant activity of lipoic acid appears to prevent free radical damage to cells and cell components. Free radical damage is most evident in cellular membranes because of the density of the molecular structure of the membranes. It is currently hypothesized that cell membrane aging leads to all of the various cellular changes seen in aging, such as decreased RNA production, decreased protein production, and faulty enzyme action.

Inflammation in skin is mediated by several active chemicals and metabolites of arachidonic acid. Arachidonic acid is oxidized by cyclo-oxygenase and lipoxygenase to active metabolites such as the leukotrienes and 5- and 12-hydroxyeicosatetraenoic acid (HETES). Within the arachidonic acid cascade, many free radicals are generated, which both perpetuate and magnify the inflammatory cascade, resulting in skin damage and manifested clinically as erythema. The redox state of the cell determines gene expression. Transcription factor nuclear factor kappa-B (NFk-B) is inactive in the cytosol under a normal redox state of the cell. When the cell undergoes oxidative stress, i.e., ultraviolet radiation, ionizing radiation, infection, and free radicals created by metabolism, the inhibitory fraction of NFk-B is dissociated from the molecule. Once the inhibitory fraction is dissociated from the NFkB molecule, it then migrates to the nucleus of the cell, begins transcription, and subsequent production of inflammatory mediators, including cytokines such as tumor necrosis factor alpha (TFα) and various interleukins, as well as many of the pro-inflammatory interleukins. These pro-inflammatory and inflammatory products of transcription then enter the cell cytoplasm effecting all parts of the cell including the mitochondria and cell membrane. Arachidonic acid is released, which is oxidized to biologically active mediators. When arachidonic acid is oxidized via the cyclooxygenase or lipoxygenase pathways, for example, prostaglandins, leukotrines, and hydroxyeicosatetraenoic acid (HETE) are produced, which cause erythema, edema, and free radical production. Lipoic acid is a powerful inhibitor of the activation of NFk-B, and therefore can act as an anti-inflammatory as well as an antioxidant. It would be useful to employ this substance in the treatment of chronic skin conditions such as rosacea.

BRIEF SUMMARY OF THE INVENTION

It is an objective of this invention to provide compositions and methods for the treatment and inhibition of rosacea.

It is another and more specific objective of the invention to provide topical compositions and methods for rosacea treatment based upon the topical application of compositions containing lipoic acid and/or lipoic acid derivatives, typically in association with a dermatologically acceptable carrier or vehicle, to skin exhibiting signs of rosacea.

These and other objectives are accomplished by the present invention, which provides compositions and methods for the treatment and/or inhibition of rosacea, which comprises topical application to skin areas exhibiting rosacea of an effective amount of lipoic acid, lipoic acid derivatives or mixtures thereof. Preferred embodiments also contain an α-hydroxy acid such as glycolic acid in addition to lipoic acid. Typical embodiments involve the topical application of compositions containing active ingredient(s) in a dermatologically acceptable carrier.

Ascorbic acid, particularly fat-soluble fatty acid esters of ascorbic acid such as ascorbyl palmitate, can, optionally, also be utilized for further enhancing the efficacy of the therapeutic or prophylactic treatment. In other embodiments, tocotrienols or derivatives thereof or vitamin E compositions enriched with tocotrienols or tocotrienol derivatives such as tocotrienol-enriched fractions of natural oils are included in the lipoic acid composition with or without an ascorbic acid ingredient.

As summarized above, in a preferred practice of the invention, effective amounts of lipoic acid (and/or derivative) is applied in admixture with glycolic or another α-hydroxy acid in a dermatologically acceptable carrier or vehicle (e.g., as a lotion, cream, ointment, soap, or the like)

so as to facilitate topical application and, in some cases, provide additional therapeutic effects as might be brought about, e.g., by moisturizing of the affected skin areas. As noted, other ingredients, particularly ascorbyl palmitate and/or tocotrienol, can be advantageously included in the compositions.

The amount of lipoic acid or derivative thereof (hereinafter referred to collectively as lipoic acid for ease of reference) necessary to treat rosacea is not fixed per se, and necessarily is dependent upon the identity and form of lipoic acid employed, the amount and type of any additional ingredients used, particularly α-hydroxy acids such as glycolic acid, but also ascorbyl esters and/or tocotrienol, the user's skin type, and the severity and extent of the patient's rosacea. In some typical embodiments, the composition contains from about 0.1% to about 7 weight %, lipoic acid or dihydrolipoic acid, more narrowly from about 0.25 to about 5 weight %. In one embodiment, about 2% to 5% lipoic acid is employed. α-Hydroxy acids are employed in concentration ranges of from about 1% to about 10%, more narrowly from about 1% to about 5%, by weight.

DETAILED DESCRIPTION OF THE INVENTION

This invention is based upon the finding that lipoic acid and/or its derivatives are useful for the treatment of rosacea.

As used herein, the term "lipoic acid" encompasses thioctic acid (1,2-dithiolane-3-pentanoic acid; 1,2-dithiolane-3-valeric acid), $C_8H_{14}O_2S_2$, formula weight 206.32. It has been variously known as acetate replacing factor, protogen A, and pyruvate oxidation factor. Elucidation of its structure and function determined that it is a co-factor for α-keto-dehydrogenase complexes, typically bound as lipoamide, that participates in acyl transfer reactions. Its reduced form, dihydrolipoic acid, is a potent sulfhydryl reductant. In aqueous systems, both LA and dihydroLA exhibit antioxidant action.

Lipoic acid derivatives include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. One particularly efficacious derivative that exhibits increased cellular uptake and biological activity useful in the practice of the invention is N,N-dimethyl,N-2-amidoethyl lipoate recently described by Sen, C.K., el al. (*Free Radical Biol. Med.*, 1998, 25:89) and called lipoic acid plus (LA-Plus). Since lipoic acid is both fat- and water-soluble, it is an advantage of the invention that it can be used in either lipid or aqueous-based compositions, and it readily crosses cellular membranes and disperses in extracellular and intracellular tissue components. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

As mentioned above, lipoic acid is fat-soluble. Therefore, lipoic acid preparations can be applied neat to skin tissue. It is an advantage of the invention that the active compound is fatty so that it physically contributes to the lubrication of affected skin areas to which it is applied.

However, only effective amounts of lipoic acid are needed to treat rosacea, so generally topical application to exposed or affected skin sites is accomplished in association with a carrier, and particularly one in which the active ingredient is soluble per se or is effectively solubilized (e.g., as an emulsion or microemulsion). Where employed, the carrier is inert in the sense of not bringing about a deactivation of the lipoic acid or derivative, and in the sense of not bringing about any adverse effect on the skin areas to which it is applied.

Suitable carriers include water, alcohols, oils and the like, chosen for their ability to dissolve or disperse lipoic acid and any other ingredient used in the treatment. Generally, even low concentrations of active ingredients in a carrier are suitable, depending upon the application regimen and adjunct ingredients employed. Many embodiments contain from about 0.1% to about 7% by weight, more narrowly from about 0.25% to about 5% by weight, LA or LA derivative. Many embodiments contain more than 1 weight % lipoic acid and/or lipoic acid derivative, e.g., from about 1.1% to about 3 to 5 weight % LA. One efficacious embodiment contains from about 2% to about 5% by weight. Examples are illustrated hereafter.

While the carrier for lipoic acid can consist of a relatively simple solvent or dispersant, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers of the scarred area. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred for skin are those carriers which are fat-soluble, i.e., those which can effectively penetrate skin layers and deliver LA to all skin layers.

As summarized above, many preferred embodiments of this invention contain at least one other ingredient in addition to lipoic acid, preferably α-hydroxy acids and/or their derivatives. As used herein, the terminology "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Most typically, α-hydroxy acids will have a basic structure of lower aliphatic compounds having from two to six carbon atoms.

The "derivatives" of these α-hydroxy acids most typically will involve derivatives related to the carboxyl functionality, i.e., wherein the hydrogen or hydroxyl portion of the carboxyl moiety is substituted by metallic ions (to form salts), alkoxy groupings (to form esters), ammonium ions (to form ammonium salts), as well as other substitution reactions and products leading to formation of corresponding lactones, anhydrides or amines. However, the derivatives may also include reactions involving the α-hydroxyl group, most notably ketone formation, to form corresponding α-keto carboxylic acids.

Among the hydroxy acids and derivative compounds useful in the present invention are hydroxy monocarboxylic acids such as glycolic acid, hydroxymethylglycolic acid, lactic acid, glucuronic acid, galacturonic acid, gluconic acid, glucoheptonic acid, α-hydroxybutyric acid, α-hydroxyisobutyric acid, α-hydroxyvaleric acid, α-hydroxyisovaleric acid, α-hydroxycaproic acid, and α-isocaproic acid. Also included are di- and tri-carboxylic hydroxy acids such as tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid. Derivatives involving keto groups include keto acids and keto esters such as pyruvic acid, methyl pyruvate, ethyl pyruvate, isopropyl pyruvate, benzoylformic acid, methyl benzoylformate, and ethyl benzoylformate. In some preferred embodiments, α-hydroxy acids having an aliphatic backbone of 2 to 3 carbons such as glycolic and/or lactic acid or their derivatives are employed. Glycolic acid is especially efficacious.

As with the other active ingredient, lipoic acid, preferred compositions contain effective amounts of α-hydroxy acids. Typcal concentrations range from about 1% to about 10% by weight, more narrowly from about 1% to about 5%, by weight α-hydroxy acid.

Fat-soluble fatty acid esters of ascorbic acid (vitamin C) may be added to the lipoic acid composition for treating rosacea in some embodiments. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

Tocotrienol may also be added to lipoic acid compositions of the invention, alone or in combination with an ascorbyl esters and/or α-hydroxy acids or their derivatives in some embodiments. The term "tocotrienol" encompasses natural and/or synthetic counterparts of tocopherol (vitamin E) that bear unsaturated tails, and include, but not limited to, α-, β-, γ-, and δ-tocotrienols, tocotrienol P25, desmethyl-tocotrienol, didesmethyl-tocotrienol, their synthetic counterparts, their counterparts having methylated or demethylated chroman rings, and mixtures thereof. The double bonds may be cis or trans or mixtures thereof.

Tocotrienol useful in compositions of the invention may be tocotrienol-enriched vitamin E preparations obtained from natural or synthetic sources, such as those obtained by removal of tocopherol from vitamin E compositions. Many embodiments employ tocotrineol isolated from natural sources such as tocotrienol-enriched fractions obtained from sunflower seed, wheat germ, bran, palm, or other vegetable oils by high performance liquid chromatography or other methods, or tocotrienol-enriched extracts obtained from barley, brewer's grains oats, and other tocotrienol-containing natural products by alcohol extraction, molecular distillation and the like. Useful tocotrienols can be tocotrienol-enriched fractions or extracts, or mixtures of these with vitamin E fractions. As used herein, the term "tocotrienols" includes all of these tocotrienol-rich fractions and extracts obtained from these natural products as well as the pure compounds and mixtures of any of these.

As with other vitamin E preparations, tocotrienol or tocotrienol-enriched preparations include those containing tocotrienol and, in some cases, tocopherol derivatives, particularly stabilized derivatives. These typically include derivatives related to the phenolic hydroxyl functionality, i.e., wherein it is acylated with an organic acid to form an ester. Examples of such stabilized tocotrienols include, but are not limited to, tocotrienol acetate, tocotrienol succinate, and mixtures thereof. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

While not wishing to be bound to any theory, it is possible that lipoic acid is efficacious in the treatment of rosacea because it is both fat- and water-soluble and readily disperses in cell membranes and other cellular components. Because of its solubility, it is sometimes referred to as a universal antioxidant. It acts as a free radical scavenger and neutralizer, and prevents the cross-linking of cell membranes that is often seen in rosacea. By the same token, LA modulation of free radicals and other oxidative species affects gene expression, including expression of nuclear factor k-B (NF-kB), nitric oxide synthetase and other mediators at all stages of proinflammation and inflammation. Lipoic acid's alteration of lipid peroxidation, protein cross-linking, growth factor stimulation, and membrane permability may explain its negative effect on the symptoms of rosacea.

Generally in the practice of the method of the invention, the composition is topically applied to the affected skin areas in a predetermined or as-needed regimen either at intervals by application of a lotion or the like, it generally being the case that gradual improvement is noted with each successive application. Insofar as has been determined based upon clinical studies to date, no adverse side effects are encountered. Though two patients reported a slight stinging within the first four days of a study, it was immediately resolved, and there were no reports or observations of irritation, erythema, irritant dermatitis or other side effects.

The following examples are presented to further illustrate and explain the present invention and should not be taken as limiting in any regard. Unless otherwise indicated, all percentages are by weight.

EXAMPLES

Lipoic acid was supplied by the Henkel Corporation and was placed into a lecithin-based oil-in-water cream at a level of 5%. In one blinded study, eight patients aged 20 to 51 diagnosed with rosasea and photographed were given the 5% lipoic cream and an identical composition containing no lipoic acid. The patients were not informed which was which, but instructed to cleanse their faces and then apply one cream to one side of their faces twice daily during the duration of the study, and apply the other cream to the other side at the same time. Patients were evaluated every two weeks. In every patient, marked improvement and a decrease in erythema was observed on the face side treated with lipoic acid after two weeks. After four weeks, erythema was even more markedly reduced on the face side to which lipoic had been applied in every patient.

In a second study, fifteen patients aged of 22 and 57 who had been diagnosed with rosacea were asked to cleanse their faces before applying to both sides of their faces a lipoic acid composition prepared as above, but containing 5% lipoic acid and 5% glycolic acid. Again, the compositions were applied twice daily. Photographs were taken of the patients' faces prior to the beginning of the study and then at the end of three months. Patients were evaluated every two weeks. Within two weeks, there was a marked decrease in the erythema associated with rosacea in every patient. There was also a decrease in pustule formation which was seen in the first two to four weeks of treatment in every patient. By the end of the study, there was a marked improvement in every patient.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for the treatment of rosacea comprising applying to the skin of a patient a composition comprising about 0.1% to about 7% of a lipoic acid ingredient, and from about 1% to about 5% of an α-hydroxy acid ingredient.

2. A method for the treatment of rosacea in accordance with claim 1 wherein said lipoic acid ingredient comprises: lipoic acid, or dihydrolipoic acid, or lipoic or dihydrolipoic acid ester, or a lipoic or dihydrolipoic acid amide, or lipoic acid plus, or a lipoic or dihydrolipoic acid salt, or a mixture of two or more thereof.

3. A method according to claim 1 wherein said α-hydroxy acid ingredient is selected from the group consisting of glycolic acid, hydroxymethylglycolic acid, lactic acid, glucuronic acid, galacturonic acid, gluconic acid, glucoheptonic acid, α-hydroxibutyric acid, α-hydroxyisobutyric acid, α-hydroxyvaleric acid, α-hydroxyisovaleric acid, α-hydroxycaproic acid, α-isocaproic acid, tartronic acid, tataric acid, malic acid, hydroxyglutaric acid, hydroxyadipic acid, hydroxypimelic acid, muric acid, citric acid, isocitric acid, saccharic acid, dihydroxymaleic acid, dihydroxytaric acid, dihydroxyfumaric acid, pyruvic acid, methyl pyruvate, ethyl pyruvate, isopropyl pyruvate, benzoylformic acid, methyl benzoylformate, ethyl benzoylformate, and mixtures of two or more thereof.

4. A method according to claim 2 wherein the lipoic acid derivative is selected from the group consisting of dihydrolipoic acid, a lipoic or dihydrolipoic acid ester, a lipoic or dihydrolipoic acid amide, a lipoic or dihydrolipoic acid salt, and mixtures thereof.

5. The method according to claim 1 wherein said the composition contains from about 0.25% to about 5% lipoic acid ingredient.

6. The method according to claim 1 wherein the composition contains from about 0.25% to about 5% lipoic acid ingredient.

7. The method according to claim 1 wherein said composition further comprises a tocotrienol, a fatty acid ester of ascorbic acid, or a mixture thereof.

8. A method for the treatment of rosacea, comprising: applying to the facial skin tissue of a patient exhibiting rosacea a composition containing about 0.1% to about 7% of a lipoic acid ingredient; and from about 1% to about 5% α-hydroxy acid ingredient; in a dermatologically acceptable carrier.

9. A method according to claim 8 wherein the said lipoic acid ingredient comprises lipoic acid, or dihydrolipoic acid, or a lipoic acid derivative, or a mixture of two or more thereof.

10. A method according to claim 8 wherein the α-hydroxy acid ingredient is selected from the group consisting of glycolic acid or lactic acid.

11. A method according to claim 8 wherein the lipoic acid derivative lipoic acid derivative is selected from the group consisting of dihydrolipoic acid, a lipoic or dihydrolipoic acid ester, a lipoic or dihydrolipoic acid amide, a lipoic or dihydrolipoic acid salt, and mixtures thereof.

12. A method according to claim 8 wherein said composition further comprises a tocotrienol, a fatty acid ester of ascorbic acid, or a mixture thereof.

13. A The method according to claim 8 wherein the composition contains from about 0.25% to about 5% lipoic acid ingredient.

\* \* \* \* \*